(12) United States Patent
Shalaby

(10) Patent No.: US 8,399,013 B2
(45) Date of Patent: *Mar. 19, 2013

(54) PARTIALLY ABSORBABLE FIBER-REINFORCED COMPOSITES FOR CONTROLLED DRUG DELIVERY

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1146 days.

This patent is subject to a terminal disclaimer.

(21) Appl. No.: 10/935,808

(22) Filed: Sep. 8, 2004

(65) Prior Publication Data

US 2005/0053639 A1   Mar. 10, 2005

Related U.S. Application Data

(63) Continuation-in-part of application No. 10/860,677, filed on Jun. 3, 2004.

(60) Provisional application No. 60/482,898, filed on Jun. 26, 2003.

(51) Int. Cl.
*A61F 6/14* (2006.01)
*A61F 13/00* (2006.01)

(52) U.S. Cl. ......... 424/432; 424/426; 424/430; 424/433

(58) Field of Classification Search .................. None
See application file for complete search history.

(56) References Cited

U.S. PATENT DOCUMENTS

| | | | |
|---|---|---|---|
| 3,920,805 A * | 11/1975 | Roseman | 424/432 |
| 4,553,972 A * | 11/1985 | Vickery | 424/430 |
| 4,629,449 A | 12/1986 | Wong | |
| 4,795,761 A | 1/1989 | Curtis-Prior et al. | |
| 4,983,393 A | 1/1991 | Cohen et al. | |
| 5,069,906 A | 12/1991 | Cohen et al. | |
| 5,176,907 A | 1/1993 | Leong | |
| 5,211,952 A * | 5/1993 | Spicer et al. | 424/426 |
| 6,086,909 A | 7/2000 | Harrison et al. | |
| 6,103,256 A | 8/2000 | Nabahi | |
| 6,127,327 A | 10/2000 | Camenzind et al. | |
| 6,299,894 B1 * | 10/2001 | Markkula et al. | 424/422 |
| 6,416,779 B1 | 7/2002 | D'Augustine et al. | |
| 6,416,780 B1 | 7/2002 | Passmore et al. | |
| 6,503,528 B1 | 1/2003 | Bieniarz et al. | |
| 6,572,874 B1 | 6/2003 | Pauletti et al. | |
| 7,416,559 B2 | 8/2008 | Shalaby | |
| 8,062,658 B2 | 11/2011 | Shalaby et al. | |
| 2004/0013730 A1 | 1/2004 | Saxena et al. | |
| 2004/0077601 A1 | 4/2004 | Adams et al. | |
| 2004/0260386 A1 | 12/2004 | Shalaby | |
| 2005/0175665 A1 | 8/2005 | Hunter et al. | |
| 2006/0240071 A1 | 10/2006 | Lerner et al. | |
| 2009/0291925 A1 | 11/2009 | Shalaby | |

FOREIGN PATENT DOCUMENTS

| | | |
|---|---|---|
| EP | 0891783 | 1/1999 |
| EP | 1827328 | 8/2011 |
| WO | 00/59559 | 10/2000 |
| WO | WO 02/15832 A1 | 8/2001 |
| WO | WO 02/15382 A1 * | 2/2002 |
| WO | 2006010097 A2 | 1/2006 |
| WO | 2006028475 | 3/2006 |

OTHER PUBLICATIONS

Cowsar et al. "Biodegradable and Non-biodegradable Fibrous Delivery Systems" International Workshop on Long-Acting Contraceptive Delivery Systems; pp. 145-163 (1984).*
Garg et al., Pharmaceutical Technology (2001) pp. 14-24.*
McCulloch & Shalaby, Tailored Polymeric Materials for Controlled Delivery Systems, ACS Symposium Series vol. 709 (1998), chapter 2.
Saxena et al, "Efficacy of nonhormonal vaginal contraceptives . . . ," Contraception, vol. 70, (2004), 213-219.
International Search Report Written Opinion dated Jun. 15, 2009.

* cited by examiner

*Primary Examiner* — Robert A Wax
*Assistant Examiner* — Jeffrey T Palenik
(74) *Attorney, Agent, or Firm* — McCormick, Paulding & Huber LLP

(57) ABSTRACT

This invention describes a partially absorbable, fiber-reinforced composite in the form of a ring, or a suture-like thread, with modified terminals for use as a controlled delivery system of at least one bioactive agent, wherein said composite comprising an absorbable fiber construct capable of providing time-dependent mechanical properties of a biostable elastomeric matrix containing an absorbable microparticulate ion-exchanger to modulate the release of the bioactive agent(s) for a desired period(s) of time at a specific biological site; this can be a vaginal canal, peritoneal cavity, scrotum, prostate gland, an ear loop or subcutaneous tissue. Such drug delivery systems can be used for the local administration of at least one bioactive agent, including those used as contraceptive, antimicrobial, anti-inflammatory and/or antiviral agents as well as for cancer treatment.

10 Claims, No Drawings

PARTIALLY ABSORBABLE FIBER-REINFORCED COMPOSITES FOR CONTROLLED DRUG DELIVERY

This application is a continuation-in-part of U.S. Ser. No. 10/860,677, filed on Jun. 3, 2004 and entitled, "Composite Absorbable/Biodegradable Rings for Controlled Drug Delivery," which claims the benefit of prior provisional U.S. Ser. No. 60/482,898, filed Jun. 26, 2003.

FIELD OF THE INVENTION

This invention deals with fiber-reinforced composite systems comprising an absorbable fiber and a partially or essentially non-absorbable matrix for use in the controlled release of one or more bioactive agent(s) at the desired biological site, which may entail intravaginal, transcutaneous, intraperitoneal, and subcutaneous implantation of such systems. For the latter two routes of administration, the controlled release system is designed to be retrievable by withdrawing the non-migrating end placed subcutaneously. The composite systems can be linear or circular and are so designed as to modulate the bioactive agent(s) release profile as well as the mechanical properties, in part, through the controlled degradation of the absorbable reinforcing fiber and any other absorbable component that may be present in the matrix.

BACKGROUND OF THE INVENTION

Prior application of the same inventor have dealt with a fiber-reinforced composite ring for the controlled release of at least one bioactive agent incorporated in a biocompatible matrix reinforced with absorbable/biodegradable fibers capable of providing the mechanical properties needed for inserting and maintaining the ring in a body cavity for a desired period of time. Such ring system can be used for the intravaginal, intraperitoneal, and subcutaneous delivery of at least one bioactive agent, including those used as contraceptives.

U.S. application Ser. No. 60/482,898 discloses a controlled drug release device comprising a partially or fully absorbable, fiber-reinforced composite ring system comprising an absorbable or non-absorbable matrix, an absorbable, reinforcing fibrous construct and an absorbable coating to provide three modes of controlling the release of bioactive agents and one mode for modulating the mechanical property of the ring in a body cavity during device functional use. For partially absorbable ring systems, the drug release is dependent initially on the diffusion rate of the drug through the matrix and the absorbable coating. As the latter degrades with time, the diffusion through the matrix prevails. Meanwhile, as the absorbable fibrous reinforcing construct undergoes degradation with time, the mechanical strength of the composite ring decreases to provide the desired mechanical strength retention profile. For a fully absorbable composite ring system, the degradation of the matrix offers an additional mode of controlling the release profile as compared with the partially absorbable counterpart. In effect, the invention of U.S. application Ser. No. 60/482,898 deals with a fiber-reinforced composite ring system for the controlled release of at least one bioactive agent comprising a biocompatible matrix reinforced with an absorbable/biodegradable fibrous construct capable of providing the mechanical properties needed for inserting and maintaining said ring in a body cavity for the desired period of time, and wherein the absorbable/biodegradable reinforcing fibers are made primarily from one or more cyclic monomer(s) including glycolide, l-lactide, $\epsilon$-caprolactone, p-dioxanone, and trimethylene carbonate.

For the partially absorbable/biodegradable composite ring controlled drug delivery system of U.S. application Ser. No. 60/482,898, the fiber-reinforced composite ring deals with the controlled release of at least one bioactive agent and comprises a biocompatible matrix reinforced with absorbable/biodegradable fibers capable of providing the mechanical properties needed for inserting and maintaining said ring in a body cavity for the desired period of time, wherein the reinforcing fibers are absorbable/biodegradable and the matrix is non-absorbable/non-biodegradable, wherein the non-absorbable matrix comprising a methacrylate polymer derived from at least one alkyl methacrylate monomer, and wherein the methacrylate polymer is derived from one or more alkyl methacrylate monomer(s) and N-vinyl pyrrolidone. Alternatively, the matrix may comprise a cyclodextrin or cyclodextrin derivative.

Obviously, the partially absorbable/biodegradable composite ring controlled drug delivery system of U.S. application Ser. No. 60/482,898 did not fully address the use of safe matrices such as silicones and polyether urethanes, which are cited in the prior art as carriers of many bioactive agents. Accordingly, this invention addresses the use of non-absorbable/biostable polyether urethane or polysiloxanes as the primary matrix component of the partially absorbable/biodegradable fiber-reinforced composite ring system comprising a drug solubility modifier for the controlled delivery of many bioactive agents including those cited in U.S. application Ser. No. 60/482,898.

SUMMARY OF THE INVENTION

The present invention deals, in general, with fiber-reinforced composite systems comprising an absorbable fiber and a partially or essentially non-absorbable matrix for use in the controlled release of one or more bioactive agent(s) at the desired biological site, which may entail intravaginal, transcutaneous, intraperitoneal, and subcutaneous implantation of such systems. For the latter two routes of administration, the controlled release system is designed to be retrievable by withdrawing the non-migrating end placed subcutaneously. The composite systems can be linear or circular and are so designed as to modulate the bioactive agent(s) release profile as well as the mechanical properties, in part, through the controlled degradation of the absorbable reinforcing fiber and any other absorbable component that may be present in the matrix.

This invention addresses a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site, wherein (1) the absorbable reinforcing fibers are formed from at least one cyclic monomer selected from the group consisting of glycolide, l-lactide, $\epsilon$-caprolactone, p-dioxanone, trimethylene carbonate, and a morpholine-2,5-dione; and (2) the biostable matrix is made of a polyether urethane elastomer or a silicone elastomer, such as copolymer polysiloxane, comprising dimethyl siloxane sequences, which can be made of at least one of the Silastic® family of silicone elastomers. It is preferred that the silicone elastomers contain evenly dispersed microparticulate silica to modulate its modulus.

A key aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site, wherein the absorbable microparticulate ion-exchanger is a carboxyl-bearing polyester based on at least one of the cyclic monomer selected from the group consisting of glycolide, l-lactide, and a morpholine-2,5-dione and said partially absorbable, fiber-reinforced composite in the form of an intravaginal ring and the biological site is the vagina, wherein the reinforcing fibers are in the form of a circularly configured construct, with protruding side loops, of multifilament or monofilament yarn and wherein the matrix comprises an absorbable/biodegradable polymer comprising ester linkages, and the parent polymer is formed from at least one cyclic monomer selected from the group consisting of glycolide, l-lactide, ε-caprolactone, p-dioxanone, trimethylene carbonate, and a morpholine-2,5-dione.

A specific aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site where (1) the biostable matrix is a silicone elastomer, such as a copolymeric polysiloxane, comprising dimethyl siloxane sequences; and (2) the absorbable microparticulate ion-exchanger is carboxyl-bearing polyester based on at least one of the cyclic monomer from the group consisting of glycolide, l-lactide, and a morpholine-2,5-dione. It is preferred that the fiber-reinforced composite ring comprises an absorbable polymeric outer coating to modulate the release of at least one bioactive agent.

It is also preferred that the composite ring comprises (1) at least one bioactive agent comprises a contraceptive agent selected from the group consisting of spermiostatic agents, spermicidal agents, hormonal agents, non-steroidal agents, viscosity modifiers capable of increasing the viscosity of vaginal mucus; (2) at least one bioactive agent having contraceptive properties, which can be a combination of ascorbic acid and iron gluconate or a non-steroidal compound, such as tanapraget, that is being evaluated clinically as an oral contraceptive with fewer side effects as compared with orally administered hormones (*Chemical & Engineering News*, Aug. 30, 2004, p. 8); (3) at least one bioactive agent having labor induction properties; (4) least one bioactive agent that is for intravaginal and transvaginal prevention or treatment of an infection selected from bacterial infections, fungal infections, viral infections and parasitic infections; (5) at least one bioactive agent that is for the treatment of cervical or ovarian cancer; (6) at least one bioactive agent that is selected from the group consisting of antifertility drugs, testosterone, testosterone precursors, spermicidal agents, sperm immobilizers, and bisphosphonate; (7) one bioactive agent that is selected from the group consisting of antiprogestinic agents, anesthetic agents, analgesic agents, anti-inflammatory agents, antimicrobial agents, antiviral agents, and antipsychotic agents; and/or (8) at least one bioactive agent that is selected from the group consisting of monoclonal antibodies, recombinant immuno-modulator vaccines, and hematopoietic growth factors.

A preferred aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site, wherein the fiber-reinforced composite is an intravaginal ring comprising a bioadhesive coating, and the matrix can be microporous or capable of being microporous during end-use.

Another specific aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site wherein said composite is in the form of a filament having a practically spherical head for outward retrieval from the biological site, wherein the biological site is (1) a human peritoneal cavity with the head being placed subcutaneously; (2) a human scrotum or prostate gland with the head being placed subcutaneously; or (3) the ear loop of an animal or human, with the head remaining ex vivo.

This invention also deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site wherein said composite is in the form of a suture-like strand for threading through a biological site, wherein the biological site is (1) an animal skin or muscle with the terminals of the suture-like filament knotted at the entrance and exit points of the skin for ease of removal after the required period of time, or (2) a human skin or muscle with the terminals of the suture-like filament knotted at the entrance and exit points of the skin for ease of removal after the required period of time.

DETAILED DESCRIPTION OF PREFERRED EMBODIMENTS

This invention deals with a controlled drug delivery device comprising a partially absorbable, fiber-reinforced system comprising a non-absorbable elastomeric matrix, an absorbable fibrous construct to modulate the device resilience and modulus with time during end-use, an absorbable microparticulate polymeric ion-exchanger to modulate the solubility of the drug through ionic interaction and/or creation of microporosity in the matrix, and preferably a non-absorbable microparticulate, inorganic filler evenly dispersed in the elastomeric matrix to increase its modulus, and preferably, an absorbable surface coating to modulate the release of drug diffusion outward from the matrix. In effect, the device is so designed to allow for modulating the initial and in-use modulus and resilience of the device by incorporating (1) an inert microparticulate inorganic filler to control the modulus; (2) an absorbable microparticulate ion-exchanger to control the initial modulus, and in-use modulus wherein the ion-exchanger absorbs/dissolves with or without ionic conjugation with active bioagent(s); and (3) an absorbable fibrous construct to control the initial resilience and modulus and modulate both properties as it absorbs during end use. Furthermore, the partially absorbable controlled drug delivery device is so designed to (1) allow the incorporation of a safe coloring additive, such as a dispersed dye, to render said device more recognizable; (2) an absorbable microparticulate ion-exchanger that is capable of interacting with the bioactive agent(s) to increase or decrease its solubility that will, in turn, affect its release profile; and (3) allow the incorporation of at least one bioactive agent that can be a contraceptive, antimicrobial, antifungal, antiviral, antibacterial, antineoplastic, and/or anti-inflammatory.

The present invention deals, in general, with fiber-reinforced composite systems comprising an absorbable fiber and a partially or essentially non-absorbable matrix for use in the controlled release of one or more bioactive agent(s) at the desired biological site, which may entail intravaginal, transcutaneous, intraperitoneal, and subcutaneous implantation of such systems. For the latter two routes of administration, the controlled release system is designed to be retrievable by withdrawing the non-migrating end placed subcutaneously. The composite systems can be linear or circular and are so designed as to modulate the bioactive agent(s) release profile as well as the mechanical properties, in part, through the controlled degradation of the absorbable reinforcing fiber and any other absorbable component that may be present in the matrix.

This invention addresses a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site, wherein (1) the absorbable reinforcing fibers are formed from at least one cyclic monomer selected from the group consisting of glycolide, l-lactide, ε-caprolactone, p-dioxanone, trimethylene carbonate, and a morpholine-2,5-dione; and (2) the biostable matrix is made of a polyether urethane elastomer or a silicone elastomer, such as copolymer polysiloxane, comprising dimethyl siloxane sequences, which can be made of at least one of the Silastic® family of silicone elastomers. It is preferred that the silicone elastomers contain evenly dispersed microparticulate silica to modulate its modulus.

A key aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site, wherein the absorbable microparticulate ion-exchanger is a carboxyl-bearing polyester based on at least one of the cyclic monomer selected from the group consisting of glycolide, l-lactide, and a morpholine-2,5-dione and said partially absorbable, fiber-reinforced composite in the form of an intravaginal ring and the biological site is the vagina, wherein the reinforcing fibers are in the form of a circularly configured construct, with protruding side loops, of multifilament or monofilament yarn and wherein the matrix comprises an absorbable/biodegradable polymer comprising ester linkages, and the parent polymer is formed from at least one cyclic monomer selected from the group consisting of glycolide, l-lactide, ε-caprolactone, p-dioxanone, trimethylene carbonate, and a morpholine-2,5-dione.

A specific aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site where (1) the biostable matrix is a silicone elastomer, such as a copolymeric polysiloxane, comprising dimethyl siloxane sequences; and (2) the absorbable microparticulate ion-exchanger is carboxyl-bearing polyester based on at least one of the cyclic monomer from the group consisting of glycolide, l-lactide, and a morpholine-2,5-dione. It is preferred that the fiber-reinforced composite ring comprises an absorbable polymeric outer coating to modulate the release of at least one bioactive agent.

It is also preferred that the composite ring comprises (1) at least one bioactive agent comprises a contraceptive agent selected from the group consisting of spermiostatic agents, spermicidal agents, hormonal agents, non-steroidal agents, viscosity modifiers capable of increasing the viscosity of vaginal mucus; (2) at least one bioactive agent having contraceptive properties, which can be a combination of ascorbic acid and iron gluconate or a non-steroidal compound, such as tanapraget, that is being evaluated clinically as an oral contraceptive with fewer side effects as compared with orally administered hormones (*Chemical & Engineering News*, Aug. 30, 2004, p. 8); (3) at least one bioactive agent having labor induction properties; (4) least one bioactive agent that is for intravaginal and transvaginal prevention or treatment of an infection selected from bacterial infections, fungal infections, viral infections and parasitic infections; (5) at least one bioactive agent is for the treatment of cervical or ovarian cancer; (6) at least one bioactive agent that is selected from the group consisting of antifertility drugs, testosterone, testosterone precursors, spermicidal agents, sperm immobilizers, and bisphosphonate; (7) one bioactive agent that is selected from the group consisting of antiprogestinic agents, anesthetic agents, analgesic agents, anti-inflammatory agents, antimicrobial agents, antiviral agents, and antipsychotic agents; and/or (8) at least one bioactive agent that is selected from the group consisting of monoclonal antibodies, recombinant immunomodulator vaccines, and hematopoietic growth factors.

A preferred aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site, wherein the fiber-reinforced composite is an intravaginal ring comprising a bioadhesive coating, and the matrix can be microporous or capable of being microporous during end-use.

Another specific aspect of this invention deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site wherein said composite is in the form of a filament having a practically spherical head for outward retrieval from the biological site, wherein the biological site is (1) a human peritoneal cavity with the head being placed subcutaneously; (2) a human scrotum or prostrate gland with the head being placed subcutaneously; or (3) the ear loop of an animal or human, with the head remaining ex vivo.

This invention also deals with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site wherein said composite is in the form of a suture-like strand for threading through a biological site, wherein the biological site is (1) an animal skin or muscle with the terminals of the suture-like filament knotted at the entrance and exit points of the skin for ease of removal after the required period of time, or (2) a human skin or muscle with the terminals of the suture-like filament knotted at the entrance and exit points of the skin for ease of removal after the required period of time.

Additional illustrative examples associated with this invention are outlined below.

EXAMPLE 1

Preparation of Acid-Terminated Polyglycolide Cation-Exchanging Microparticulate (PG-61)

Glycolide was polymerized in the presence of glycolic acid and stannous octanoate to produce low molecular weight, hydrolytically degradable polyester PG-61, as described in U.S. Pat. No. 6,413,539. Purification and reduction in size of PG-61 was also conducted as per U.S. Pat. No. 6,413,539 teaching.

EXAMPLE 2

Preparation of 95/5 ε-Caprolactone/Glycolide Copolymer Coating (CT-1)

The CT-1 copolymer was prepared by the copolymerization of ε-caprolactone (0.625 mole) with glycolide (32.3 mmole) in the presence of glycolic acid (3.756 mmole) as the initiator and stannous octanoate (0.1247 mmole as 0.2M solution in toluene) as the catalyst. The polymerization was conducted in a mechanically stirred reactor under a dry nitrogen atmosphere at 150° C. for 6.25 hours. At the conclusion of the polymerization, as determined by GPC, traces of unreacted monomer were removed by distillation under reduced pressure. The composition of the purified polymer was verified by IR and NMR. The polymer was shown to melt at 55° C. as determined by DSC.

EXAMPLE 3

Preparation of Partially Absorbable, Fiber-Reinforced Composite Silicone Elastomers as an Intravaginal Ring—General Method Listed below are the components of an active matrix that are mixed and introduced into a closed, 2-part Teflon mold having a ring-type cavity (ID=4.3 cm, OD=5.5 cm), an inlet for introducing the reactants, and an outlet to exit displaced dry nitrogen used in pre-purging the dry mole. A circular construct (outside diameter=4.9 cm) was made as a braided multifilament yarn (with an average single filament diameter of 15 micron) having side loops was placed centrally (by virtue of the side loops) into the cavity of the lower component of the mold to allow for equidistant placement between the OD and ID of the curved ring system. A fraction of the components listed below, which have been mixed under nitrogen, was charged into the lower half of the open mold under a nitrogen atmosphere. The top part was then placed on the lower part, and the mold was closed and mechanically secured. The remaining fraction of the mixed components was then injected into the mold through the feed port.

List of Mixed Matrix Components and Filler

Two-component Silastic®

Fibrous Construct

Microparticulate Cation-exchanger (from Example 1)

Bioactive agent(s)

The charged mold is heated at 80° C. for the required period of time. At the conclusion of the heating cycle, the ring was removed and coated, if so needed, with 95/5 poly(caprolactone-co-glycolide)(from Example 2) by dipping in a 5 percent solution of methylene chloride followed by drying. The ring is then used for testing in a phosphate buffered solution at 37° C. as a function of time for: (1) the drug release profile at pH 4.5; and (2) compressibility retention profile, as measured in terms of the radial deformation force (RDF) that is required to attain a predetermined degree of deformation, using an MTS Universal Tester (858 MiniBionix) in the compression mode.

EXAMPLES 4 to 6

Preparation of Partially Absorbable Fiber-Reinforced Composite of Silicone Elastomers as Contraceptive Intravaginal Rings: Specific Examples Uncoated ring systems I to III were prepared following the same general procedure described in Example 3 and using a mixture of ascorbic acid, iron gluconate, and PG-61 (from Example 1). The components used in preparing these rings and the curing conditions are summarized in Table I.

TABLE I

Composition Data and Curing Conditions for Intravaginal Rings I to III

| | Example Number | | |
|---|---|---|---|
| | 4 | 5 | 6 |
| Ring Number | I | II | III |
| Silastic ® matrix: | | | |
| Type | Q7-6830 | Q7-6830 | Q7-4840 |
| Weight of Component A, g | 2.1 | 2.0 | 1.85 |
| Weight of Component B, g, | 2.1 | 2.0 | 1.85 |
| Fiber-reinforcing Construct[a], mg | 150 | 300 | 300 |
| Cation-exchanger[b], mg | 171 | 165 | 152 |
| Active Ingredients: | | | |
| Ascorbic acid, mg | 343 | 330 | 304 |
| Fe gluconate, mg | 320 | 330 | 304 |
| Dye (D&C Violet #2), mg | 5 | 5 | 3.8 |
| Curing Cycle | | | |
| Temperature/Time, ° C./hour | 80/15.5 | 80/4 | 80/4 |

[a]Braided copolymeric l-lactide braided suture made of segmented 88/12 l-lactide/ trimethylene carbonate as described in U.S. Pat. No. 6,342,065.
[b]PG-61 from Example 1

EXAMPLE 7

Preparation of Partially Absorbable Fiber-Reinforced Composite of Silicone Elastomers as Antimicrobial Intravaginal Ring IV Uncoated Ring IV, was prepared following the same general procedure described in Example 3 and using Metronidazole as the bioactive agent. The components used in preparing this ring and curing conditions are summarized in Table II.

TABLE II

Composition Data and Curing Conditions of Intravaginal Ring IV

| Ring Number | IV |
|---|---|
| Ring Composition Silastic ® matrix: | |
| Type | Q7-4840 |
| Weight of Component A, g | 2.3 |
| Weight of Component B, g, | 2.3 |
| Fiber-reinforcing Construct[a], mg | 300 |
| Cation-exchanger[b], mg | 7 |
| Active Ingredient, Metronidazole, mg. | 137 |
| Dye (D&C Violet #2), mg | 3.8 |
| Curing Cycle | |
| Temperature/Time, ° C./hour | 80/4 |

[a]Braided copolymeric l-lactide braided suture made of segmented 88/12 l-lactide/ trimethylene carbonate as described in U.S. Pat. No. 6,342,065.
[b]PG-61 from Example 1

EXAMPLE 8

Radial Deformation Force (RDF) Measurement for Evaluating Ring Compressibility: General Method The initial compressibility of the ring and percent retention, during incubation in a phosphate buffered solution to simulate the biological environment, was measured in terms of the force (in Newtons) required to deform the ring, radially, by 2.54 cm. The initial compressibility was conducted by placing the ring in the lower component of the sample holder of an MTS Universal Tester (MiniBionix, Model 858) and measuring the force required to deform the upper part of the ring, radially, for a distance of 2.54 cm through the downward movement at a rate of 1 mm/sec, of the free, flat upper component of the sample holder.

To determine the percent retention of ring incubated in a buffered solution at pH 4.5 and 37° C., the test ring was removed at the desired period, wiped with tissue paper to remove excess moisture, and the force of deformation at time "t" (Ft) was measured as noted above for the initial deformation force (Fo) testing. The percent strength retention, in terms of decrease of the RDF, was calculated as follows:

% RDF retention=$(Fo-Ft \div Fo) \times 100$.

TABLE III

Typical Radial Deformation Force (RDF) Values and In Vitro Retention Data of Partially Absorbable Intravaginal Rings

| Ring Number | From Example | RDF, N | In vitro[a] Retention of RDF (% @ day) |
|---|---|---|---|
| II | 5 | 1.66 | 82/2 |
| III | 6 | 2.26 | 79/14 |
| IV | 7 | 1.52 | 89/10 |

[a]Using a phosphate buffer at pH 4.5 and 37° C.

EXAMPLE 9

Determination of Daily and Cumulative In Vitro Release Rates of Ascorbic Acid and Ferrous Gluconate from Eluates of a Typical Contraceptive Ring System I. Outline of the Experimental Procedure The procedure consists of: (1) cutting pieces of a typical ring system (as in Examples 10, 12, 19, 20, and 21) and recording the weight (pieces are placed in separate, labelled Petri dishes); (2) placing the pieces of the ring containing ferrous gluconate into a shaker containing 5 mL of phosphate buffered saline or water to Petri dishes, sealing with parafilm, and incubating at 37° C. overnight; (3) collecting the eluate and measuring the volume each day, then transferring the ring pieces to a new Petri plate in 5 mL of fresh phosphate buffered saline and following Step (2) above; (4) continuing the above procedure daily for 2-days, then drying the residual matrix and recording the final weight; and (5) determining the amount of ascorbic acid and ferrous gluconate in each daily collection of the eluate.

II. Determination of Ascorbic Acid

A. Principle: In this procedure, ascorbic acid is oxidized to dehydroascorbic acid and the latter is coupled with 2,4-dinitrophenylhydrazine. The coupling reaction forms the 2,4-dinitrophnylosazone of dehydroascorbic acid, a light brown crystalline compound. When treated with 85% $H_2SO_4$, the osazone is rearranged to form a reddish colored compound, which absorbs maximally at 500 to 550 mµ. It is a highly stable product under the conditions used and is well suited for calorimetric measurement.

B. Preparation of Reagents:

Reagents used included (1) trichloroacetic acid solutions, 4%; (2) 2,4-dinitrophenylhydrazine reagent (2.0 g of 2,4-dinitrophenylhydrazine were dissolved in 100 mL 9N $H_2SO_4$ [1 part of concentrated $H_2SO_4$ plus 3 parts water], 4 g of reagent thiourea were added, shaken occasionally, dissolved, filtered and then refrigerated; and (3) ascorbic acid solutions.

Stock Solution: Ascorbic acid of the highest purity (12.5 mg) is dissolved in 50 mL of 0.5% oxalic acid. This solution is oxidized by adding one teaspoon (or 1 g) of acid-washed Norite (activated carbon) per 50 mL, shaking thoroughly, and filtering through Whatman No. 42 filter paper. One mL of this solution contains 10 µg of dehydroascorbic acid. Keep refrigerated.

Standard Solution of Dehydroascorbic Acid: To prepare the Standard Curve Solutions, dilute the dehydroascorbic stock solution with 4.0% trichloroacetic acid. The dilutions will serve for a range of 20 to 200 mg of ascorbic acid per liter of solution.

C. Procedure:

Two mL of Norite filtrate of unknowns, 2 mL of the dehydroascrobic acid standard solution, and 2 mL of 4% TCA (control tube) are added to glass tubes. Then 0.5 mL of 2,4-dinitrophenylhydrazine reagent is added to each tube. The tubes are placed in a constant temperature water bath at 37° C. The tubes are kept immersed in the bath for approximately 1.5 hours, removed, and subsequently placed in a beaker of ice water containing generous quantities of ice. To each of the tubes in the ice water bath is added slowly 2.5 mL of 85% $H_2SO_4$. The tubes are shaken under the ice water to obtain complete mixing and are then removed to a rack. After 30 minutes, the tubes are wiped and cleaned to record the absorbance in a colorimeter, using 540 mµ filter. To take the reading, the control tube is used to set the colorimeter at 100% transmittance or zero absorbance.

III. Determination of Ferrous Gluconate

A. Materials and Methods: The samples assayed for ferrous gluconate were taken from the solutions, which contained the Ovaprene ring over various periods of time. Reagents used for the assay were phosphate buffered saline, pH 7.4 (PBS), 1,10-Phenanthroline, sodium acetate (anhydrous), and bromophenol blue dye (pH 3.0-4.6) (Sigma), hydroquinone and acetic acid (Aldrich), and ferrous gluconate (Alfa Aesar). Spectronic 20 Genesys™ Spectrophotometer was used to read the solution absorbance.

The reagents for the assay were prepared as follows:
1. Phosphate buffered saline (PBS)-add one packet to 1000 ml of distilled water.
2. 1% solution of hydroquinone is prepared with distilled water.
3. 0.5% solution of 1,10-Phenanthroline is prepared with distilled water and sodium acetate-acetic acid solution added to 4% final volume (Keep in dark and discard if any color develops).
4. Sodium acetate-acetic acid buffer solution (pH 4.0)- dissolve 27 g of anhydrous sodium acetate in 50 ml of distilled water. Then add 24 ml of acetic acid and bring to a final volume of 100 ml with distilled water.
5. 1 mM solution of ferrous gluconate standard is prepared with PBS.
6. A 1 mg/ml solution of bromophenol blue dye is prepared with distilled water.

B. Procedure: For the ferrous gluconate standard curve, 1 mM ferrous gluconate standard solution was diluted with PBS to produce the following final concentrations: 0.75 mM, 0.5 mM, and 0.25 mM.

The assay was performed by adding 600 µl of the standard curve solutions and 600 µl of each ring buffer to be assayed to 5-ml glass tubes. The control tube was 600 µl of PBS. Using a Pasteur pipette one drop f bromophenol blue and one drop of sodium acetate solution was added to each tube, followed by the addition of 1 ml of 1% hydroquinone and 1 ml of 0.5% 1,10-Phenanthroline. The tubes were gently vortexed and incubated at 50° C. for 2 hr. Using a spectrophotometer, the transmittance for each tube was read at 408 nm.

EXAMPLE 10

Determination of the Initial Release Profile of Metronidazole from Antimicrobial Ring IV Specimens of Ring IV made as described in Example 7 were placed in a phosphate buffer at 37° C. and pH 4.5. The concentration of released Metronidazole was determined over an eight-day period. Analysis of Metronidazole was conducted on day 2, 3, 6, and 8 and the buffer was replaced with fresh aliquots at each of these periods. The cumulative percent release data are summarized below:

|  | Study Period, day | | | |
| --- | --- | --- | --- | --- |
|  | 2 | 3 | 6 | 8 |
| Cumulative % Release | 4.3 | 5.2 | 7.4 | 8.8 |

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. An intravaginal ring for the controlled delivery of a bioactive agent, said ring comprising a) a copolymeric silicone matrix and b) an absorbable fiber construct,
   wherein said copolymeric silicone matrix further comprises a bioactive agent and an absorbable microparticulate ion-exchanging polymer which modulates the release of said bioactive agent,
   wherein said bioactive agent is a non-hormonal contraceptive,
   wherein said absorbable fiber construct provides time-dependent mechanical properties, and wherein said non-hormonal contraceptive is incorporated within said matrix and not within the absorbable fiber construct.

2. The intravaginal ring of claim 1, wherein said absorbable fiber construct is formed from at least one cyclic monomer.

3. The intravaginal ring of claim 2 wherein said cyclic monomer is selected from the group consisting of glycolide, l-lactide, ε-caprolactone, p-dioxanone, trimethylene carbonate, and a morpholine-2,5 dione.

4. The intravaginal ring of claim 1, wherein said absorbable fiber construct is further coated with a composition comprising ε-caprolactone and glycolide.

5. The intravaginal ring of claim 1 wherein said silicone matrix comprises copolymeric polysiloxane having dimethyl siloxane sequences.

6. The intravaginal ring of claim 1 wherein said absorbable fiber construct is a multifilament yarn.

7. The intravaginal ring of claim 1 wherein said microparticulate ion-exchanging polymer comprises at least one cyclic monomer selected from the group consisting of glycolide, l-lactide and a morpholine-2,5 dione.

8. The intravaginal ring of claim 1, wherein said bioactive agent comprises iron gluconate.

9. The intravaginal ring of claim 1, wherein said bioactive agent comprises ascorbic acid.

10. The intravaginal ring of claim 1, wherein said ring further comprises a dye.

* * * * *